(12) United States Patent
Ovsyanko

(10) Patent No.: US 8,941,966 B2
(45) Date of Patent: Jan. 27, 2015

(54) MAGNETIC SYSTEM FOR PARTICLE ATTRACTION IN A PLURALITY OF CHAMBERS

(75) Inventor: Mikhail Ovsyanko, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 127 days.

(21) Appl. No.: 13/820,754

(22) PCT Filed: Sep. 5, 2011

(86) PCT No.: PCT/IB2011/053863
§ 371 (c)(1),
(2), (4) Date: Mar. 5, 2013

(87) PCT Pub. No.: WO2012/035462
PCT Pub. Date: Mar. 22, 2012

(65) Prior Publication Data
US 2013/0170089 A1     Jul. 4, 2013

(30) Foreign Application Priority Data
Sep. 17, 2010   (EP) .................................. 10177267

(51) Int. Cl.
*H01H 47/00* (2006.01)
*H01F 7/06* (2006.01)
*G01N 35/00* (2006.01)

(52) U.S. Cl.
CPC ............ *H01F 7/064* (2013.01); *G01N 35/0098* (2013.01)
USPC ....................................................... 361/143

(58) Field of Classification Search
USPC ........................................................ 361/143
See application file for complete search history.

(56) References Cited

U.S. PATENT DOCUMENTS

| | | | |
|---|---|---|---|
| 4,738,773 A | 4/1988 | Mueller-Ruchholtz et al. | |
| 6,514,415 B2 | 2/2003 | Hatch et al. | |
| 8,283,912 B2 * | 10/2012 | Nieuwenhuis et al. | 324/204 |
| 8,411,274 B2 * | 4/2013 | Verschuren et al. | 356/445 |
| 8,520,211 B2 * | 8/2013 | Schleipen et al. | 356/442 |
| 2005/0181508 A1 | 8/2005 | Fredriksson et al. | |
| 2007/0214900 A1 | 9/2007 | Porat et al. | |
| 2009/0035746 A1 | 2/2009 | Ehben et al. | |
| 2010/0188076 A1 | 7/2010 | Kahlman et al. | |

FOREIGN PATENT DOCUMENTS

| | | | |
|---|---|---|---|
| WO | 9313400 | A2 | 7/1993 |
| WO | 9615440 | A1 | 5/1996 |
| WO | 2005010542 | A2 | 2/2005 |
| WO | 2005010543 | A1 | 2/2005 |
| WO | 2008094198 | A2 | 8/2008 |

(Continued)

*Primary Examiner* — Stephen W Jackson

(57) ABSTRACT

The invention relates to a magnetic sample-processing device, particularly a sensor device (100), that comprises two electromagnets (110, 120) for generating a magnetic field (B) in a first and a second sample chamber (SC1, SC2) located adjacent to each other in an x-direction. The poles of the electromagnets are disposed below the first and the second sample chamber (SC1, SC2), respectively, next to each other in a perpendicular y-direction. Moreover, the electromagnets are individually controlled by a control unit (130). In a preferred embodiment, the distance between the electromagnets (110, 120) in x-direction is so large that magnetic cross talk can be neglected. In another embodiment, said distance is close, and the electromagnets are operated in a synchronized way.

12 Claims, 5 Drawing Sheets

(56) References Cited

FOREIGN PATENT DOCUMENTS

| WO | 2008155723 | A1 | 12/2008 |
| WO | 2009040721 | A1 | 4/2009 |
| WO | 2009125339 | A2 | 10/2009 |
| WO | 2010049883 | A1 | 5/2010 |

* cited by examiner

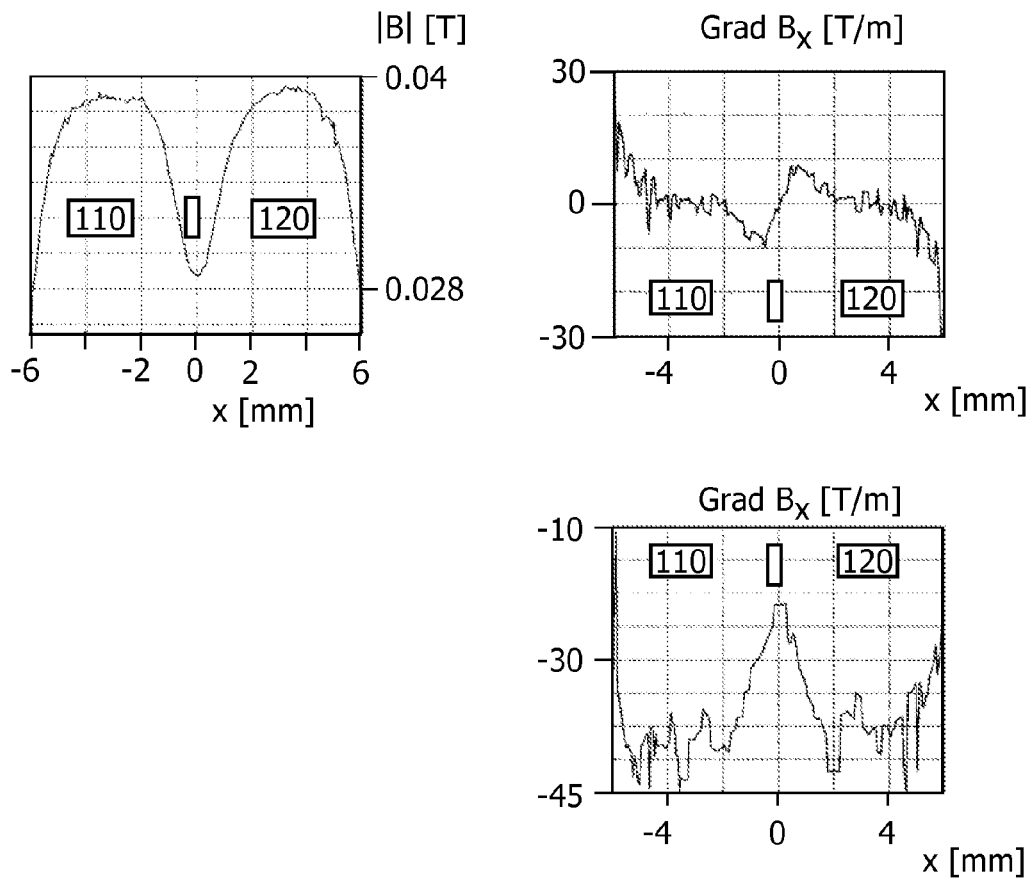
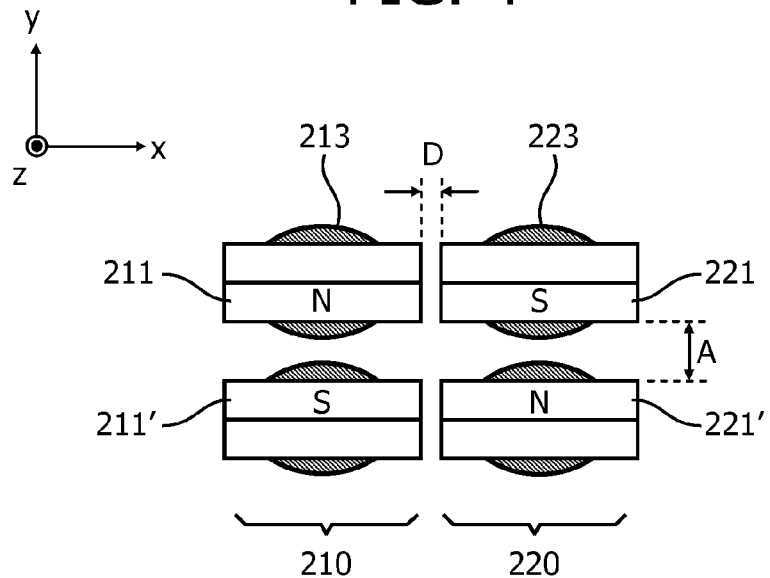
FIG. 5

MAGNETIC SYSTEM FOR PARTICLE ATTRACTION IN A PLURALITY OF CHAMBERS

FIELD OF THE INVENTION

The invention relates to a magnetic sample-processing device, particularly a biosensor, comprising means for generating a magnetic field in a first and second sample chamber that are located adjacent to each other. Moreover, it relates to a method for processing a sample in such a device.

BACKGROUND OF THE INVENTION

From the WO 1993/013400 A1, a washing/aspiration system for magnetic particles is known that comprises a plurality of permanent magnets arranged with their poles in an array. A sample container with a plurality of adjacent wells that are arranged in the same pattern as the magnetic poles is moved across the array of poles to consecutively execute certain magnetic manipulations in said wells.

SUMMARY OF THE INVENTION

Based on this background it was an object of the present invention to provide alternative means for magnetically processing a sample, particularly for attracting magnetic particles in a bioassay to a sensing surface.

This object is achieved by a magnetic sample-processing device according to claim 1 and a method according to claim 2. Preferred embodiments are disclosed the dependent claims.

The magnetic sample-processing device of the present invention shall comprise means for generating magnetic fields ("actuation fields") in a first and a second sample chamber, wherein said chambers are located adjacent to each other in a direction that will in the following be called "x-direction". A sample chamber is typically an empty cavity, particularly an open cavity, a closed cavity, or a cavity connected to other cavities by fluid connection channels. The magnetic sample-processing device shall comprise the following components:

a) A first electromagnet with a first pair of poles that can be disposed below the first sample chamber such that said poles are aligned in a direction substantially perpendicular to the x-direction, said perpendicular direction being called "y-direction" in the following. Here and in the following, the term "below" etc. shall indicate a relative arrangement of components but not imply a particular orientation with respect to gravity.

b) A second electromagnet with a second pair of poles that can be disposed below the second sample chamber next to each other in said y-direction (wherein this arrangement shall be possible while the first electromagnet is disposed as described above in item a).

c) A control unit for controlling the first and the second electromagnet individually. The control unit may for example be realized in dedicated electronic hardware, digital data processing hardware with associated software, or a mixture of both. It will typically be connected to be electromagnets by wire, though a wireless communication is possible, too.

It should be noted that the design principle of the magnetic sample-processing device of course also applies to more than two sample chambers and associated electromagnets. Moreover, the sample chambers may be considered as parts of the device or as separate components.

The invention further relates to a corresponding method for processing a sample with a sample-processing device, particularly a device of the aforementioned kind, in a first and a second sample chamber that are located adjacent to each other in an x-direction. The method comprises the following steps, which can be executed in the listed or any other appropriate order:

a) Disposing below the first sample chamber a first electromagnet with a first pair of poles which are arranged next to each other in a y-direction that is substantially perpendicular to the x-direction.

b) Disposing below the second sample chamber a second electromagnet with a second pair of poles which are arranged next to each other in the y-direction.

c) Controlling the first and the second electromagnet individually to generate a magnetic field in the first and/or the second sample chamber.

The described magnetic sample-processing device and the method have the advantage that, by using electromagnets which are specifically assigned to different sample chambers and which can individually be controlled, they allow for the simultaneous execution of different actuation protocols in the sample chambers.

In the following various preferred embodiments of the invention will be described that relate to both the sample-processing device and the method described above.

The sample chambers will usually be filled with samples that shall be processed. To facilitate this filling and to allow for the disposal of a contaminated sample chamber, the first and second sample chambers are preferably hosted in an exchangeable cartridge.

In another preferred embodiment of the invention, the first and second sample chamber are physically separated from each other, for example by an intermediate barrier or wall that prevents the free exchange of fluids between the two chambers. Such a physical separation provides additional means to execute completely separate processes in the two sample chambers.

In general, the design of the electromagnets may be arbitrary as long as two poles are provided that can be located below a sample chamber. In a preferred embodiment, the first and/or the second electromagnet comprises a core with a horse-shoe shape, wherein the free tips of the horse-shoe constitute the poles that can be located beneath a sample chamber. The material of the core will typically be a ferromagnetic material like iron. The core allows to guide the magnetic field, which is generated in the core for example by a coil wound around it at a convenient location, to the place where the field shall be applied.

In the xy-plane that is defined by the x-direction and the y-direction, the four poles of the electromagnets are arranged in a pattern that generally constitutes a trapezoid. Preferably, the distance between two poles of a pair in y-direction is the same for the two electromagnets, yielding the particular arrangement of a parallelogram, most preferably of a rectangle.

There are two preferred alternative designs with respect to the distance between the electromagnets in x-direction, more precisely with respect to the distance between the pairs of poles of the electromagnets:

In a first design, the pair of poles of the first electromagnet is separated in x-direction from the pair of poles of the second electromagnet by a distance "D" that is larger than the distance "A" measured in y-direction between the poles of one pair (if this inter-pole distance A should have different values for the two electromagnets, the relation shall hold for the average value). In a particularly preferred embodiment, the distance D in x-direction between the pairs of poles shall be larger than about 1.2 mm. This first arrangement has the advantage that the magnetic interaction between the poles of one and the same electromagnet is stronger than the interaction between the two poles of different electromagnets. Magnetic cross talk between the magnetic fields in different sample chambers is thus reduced to a level that can practically be neglected.

In a second design, the pair of poles of the first electromagnet is separated in x-direction from the pair of poles of the second electromagnet by a distance "D" that is less than about half the distance "A" between the poles of one pair (if this inter-pole distance A should have different values for the two electromagnets, the relation shall hold for the average value). In a particularly preferred embodiment, the distance D in x-direction between the pairs of poles shall be less than about 0.5 mm. In this arrangement, a pole of the first electromagnet will find a pole of the second electromagnet in closer proximity than its own counter-pole. Hence there will be a considerable crosstalk between the magnetic fields of the two electromagnets. With the mentioned design parameters, this drawback can however be compensated, as the crosstalk gets a well-defined influence that can purposefully be used.

In a further development of the invention, the (closely) neighboring poles of the different electromagnets are operated to have, in a temporal average, opposite polarities for a predetermined percentage of time. In this way the interaction between an "edge effect" and a "crosstalk" that occur in the middle between the two electromagnets can be adjusted to achieve a desired overall behavior. This approach is particularly useful in combination with the aforementioned embodiment, in which the electromagnets are disposed so close to each other that there is a considerable crosstalk between neighboring poles. It should be noted that the "predetermined percentage of time" may cover the whole range from 0% (i.e. neighboring poles of the different electromagnets are always operated with the SAME polarity) to 100% (i.e. neighboring poles of the different electromagnets are always operated with OPPOSITE polarity). Moreover, said percentage may dynamically be changed during an assay if desired.

In the aforementioned embodiment, the operation protocols for the first and the second electromagnet are preferably synchronized with respect to the switching of magnetic polarity. With respect to other parameters, for example the magnitude of the generated magnetic field, the two electromagnets may be operated asynchronously.

In general, the magnetic sample-processing device and the method may serve any purpose in which magnetic fields in two sample chambers are required. A particularly preferred application is the detection of magnetic particles in a sample wherein such particles are moved (actuated) within the respective sample chambers by the magnetic fields, particularly attracted towards (or away from) a sensing surface. In this embodiment, the sample-processing device comprises a sensor module for detecting particles in the sample chambers, particularly at a sensing surface adjacent to the electromagnets.

In the aforementioned case, the sensor module may comprise an optical, magnetic, mechanical, acoustic, thermal and/or electrical sensor element. A magnetic sensor element may particularly comprise a coil, Hall sensor, planar Hall sensor, flux gate sensor, SQUID (Superconducting Quantum Interference Device), magnetic resonance sensor, magneto-restrictive sensor, or magneto-resistive sensor of the kind described in the WO 2005/010543 A1 or WO 2005/010542 A2, especially a GMR (Giant Magneto Resistance), a TMR (Tunnel Magneto Resistance), or an AMR (Anisotropic Magneto Resistance). An optical sensor element may particularly be adapted to detect variations in an output light beam that arise from a frustrated total internal reflection due to magnetic particles at a sensing surface.

In case of an optical sensor module, this may particularly comprise a light source which can simultaneously illuminate sensing regions of both the first and the second sample chamber.

Similarly, an optical sensor module may preferably comprise a light detector that can simultaneously measure light coming from the sensing regions of both the first and the second sample chamber. Such a light detector may particularly be an image sensor, for example of a digital camera.

In the above embodiments with a light source and a light detector, respectively, one component is used to optically process (i.e. illuminate or image) both sample chambers simultaneously. To this end, the field of view of this component must be large enough. This requirement can more readily be fulfilled in the above second design alternative in which the electromagnets are located close to each other.

The invention further relates to the use of the device described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which:

FIG. 4 shows recordings of the magnetic field and its gradients for the arrangement of FIG. 1;

FIG. 5 shows a top view onto the electromagnets of a sample-processing device according to a second embodiment of the invention, having a smaller distance between the electromagnets;

Like reference numbers or numbers differing by integer multiples of 100 refer in the Figures to identical or similar components.

DESCRIPTION OF PREFERRED EMBODIMENTS

The invention will in the following be described with respect to its application in a biosensor, though it can be used in other setups and for other purposes, too.

Figure 1:
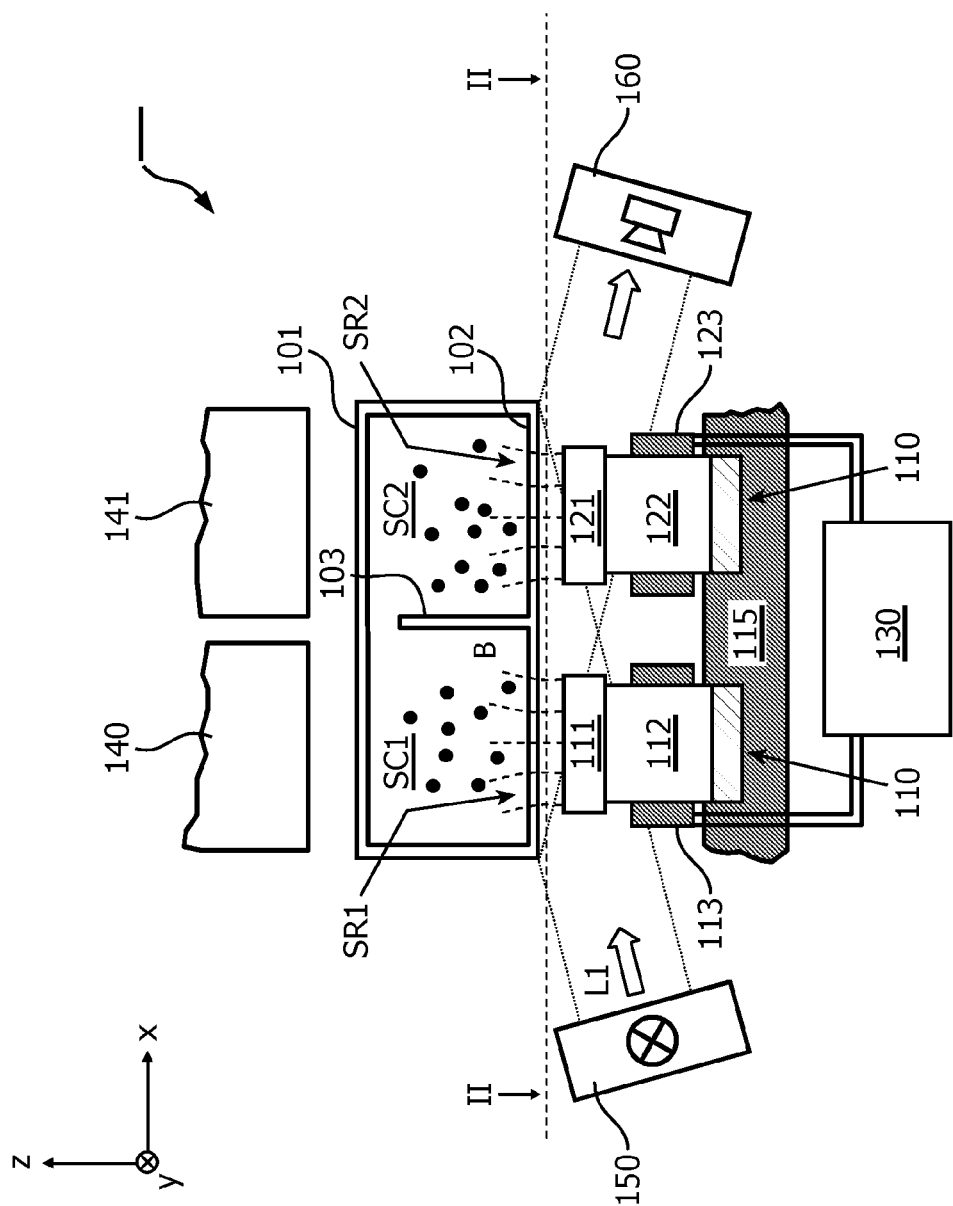
FIG. 1 shows a schematic section through a sample-processing device according to a first embodiment of the invention, having a larger distance between the electromagnets.

FIG. 1 shows a cross section through a biosensor 100 that is designed according to the present invention. The sensor device 100 comprises a (typically exchangeable/disposable) container or cartridge 101 having (at least) two sample chambers SC1 and SC2 that are separated by a wall 103. The bottom of the sample chambers is constituted by a sensing surface 102, giving rise to two separate sensing regions SR1 and SR2 in the two sample chambers. A sample (or, alternatively, two different samples) with magnetic particles 1 can be provided in the sample chambers.

The sensor device 100 further comprises two electromagnets 110 and 120 with poles 111, 121 (and 111', 121', not visible), cores 112, 122, and coils 113, 123 for generating a magnetic field B in the sample chambers SC1, SC2. Moreover, it comprises a sensor module with a light source 150 and a light detector, e.g. an image sensor 160, for measuring frustrated total internal reflection (FTIR) of an input light beam L1 at the sensing surface 102. Further details of an FTIR measurement procedure may be found in the WO 2008/155723 A1, which is incorporated into the present text by reference. Instead of using FTIR, other localized detection means may be used, too, for example the application of a wedge-like structure (not shown) at the sensing surface (cf. WO 2009/125339 A2).

During activity of the electromagnets 110, 120, magnetic particles 1 (e.g. superparamagnetic beads) are collected from the sample volume by the attractive force exerted by the field gradient Grad $B_z$ in z-direction. When reaching the sensor surface 102, the magnetic particles 1 can specifically bind to binding sites, e.g. to specific antibodies on the surface (at least particular magnetic particles, e.g. those that have previously bound to a target molecule in the sample). Here an increase in particle density results in an increased optical signal in the light detector 160.

A possible approach to detect a number of different target molecules simultaneously is to use a plurality of separate detection spots on a sensor surface covered with different specific antibodies. The presence of target molecules on the detection spots is then indicated by magnetic labels that are bound to the target molecules. The concentration of magnetic beads is optically measured for each of the individual spots by imaging the spots on a camera sensor. As magnetic actuation is used to accelerate the assay by attracting magnetic particles to the sensor surface and to perform a magnetic washing step, the detection spots have to be located in the "sweet-spot" of the magnet. This can be achieved by using separate magnets for each sample chamber, as realized in the sensor device 100 of FIG. 1. It is advantageous to have the individual detection spots in fully separated measurement chambers so that the assay conditions can be optimized for each assay individually.

Figure 2:
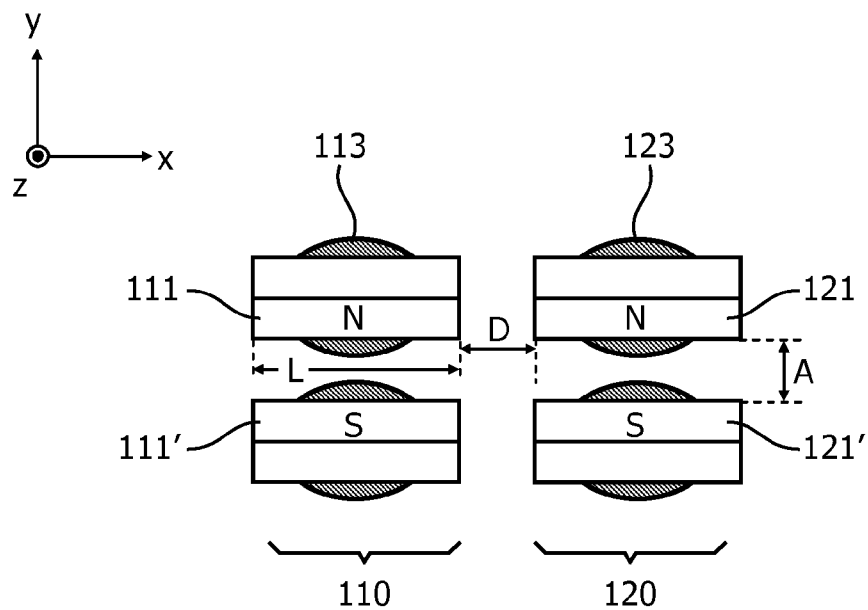
FIG. 2 shows a top view onto the electromagnets of FIG. 1.

FIG. 2 shows a top view onto the poles 111 and 111' of the first electromagnet 110 and the poles 121 and 121' of the second electromagnet 120, which are located below the sensing surface 102 (see dashed line II-II indicating the viewing plane in FIG. 1). The poles are arranged in the xy-plane in a rectangular pattern, wherein the distance (in y-direction) between poles of the same electromagnet, e.g. poles 111 and 111', is denoted as "A", and the distance (in x-direction) between neighboring poles of different electromagnets, e.g. poles 111 and 121, is denoted as "D".

Figure 3:
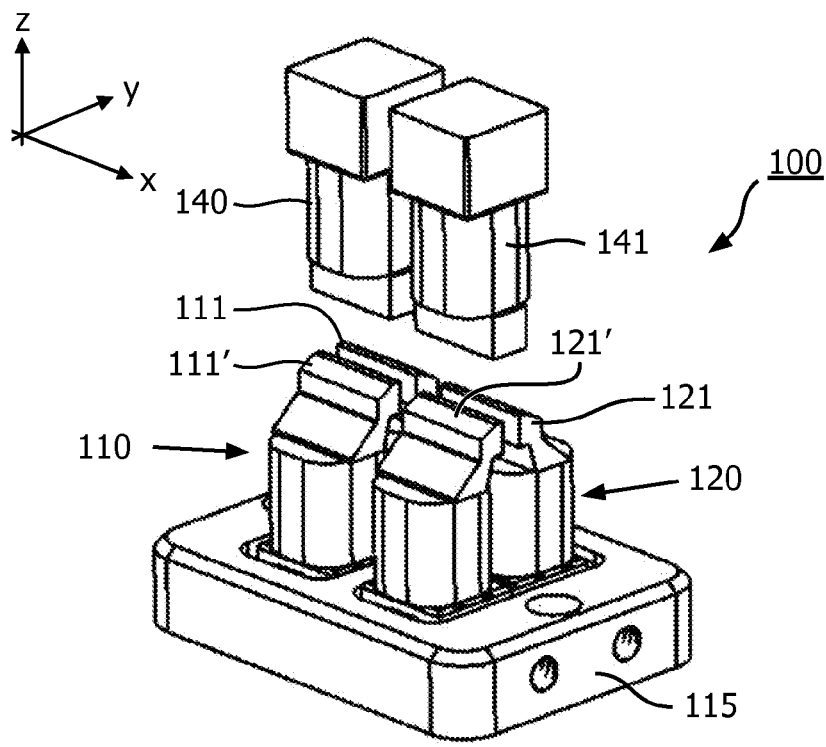
FIG. 3 shows the electromagnets of FIG. 1 separately in a perspective view.

FIG. 3 shows a separate perspective view of the electromagnets 110 and 120, which are mounted on a common platform. Moreover, the Figure shows electromagnets 140, 141 that can be located above the sample chambers for magnetic washing procedures.

The close neighborhood of the two electromagnets 110, 120 implies that crosstalk effects between the generated magnetic fields have to be taken into account. This can be done by a proper choice of the mentioned distances A and D, as will be explained in more detail in the following.

In the first embodiment of the invention that is illustrated in FIGS. 1 to 4, the distance D in x-direction between the poles of different electromagnets 110 and 120 is chosen to be large enough that the magnetic fields B generated in the respective sample chambers SC1 and SC2 are (at least for practical purposes) fully independent. In a typical embodiment, the distance A between the poles of the same electromagnet in y-direction may be about 1 mm, and the length L of a single pole (x-direction) may be about 5 mm. For these values, the distance D between the poles of the electromagnets may be chosen to be about 1.6 mm or larger, as the mutual magnetic influence of the electromagnets turns out to be negligible in this case. It should be noted that a wide optical system with a field of view of about 12 mm is required in this embodiment to completely cover both sample chambers SC1 and SC2.

FIG. 4 shows for the described embodiment exemplary measurement results of magnetic field parameters in the sample chambers in dependence on the lateral position x, namely the absolute value of the magnetic flux B (top left), and its gradients in x-direction (top right) and z-direction (bottom).

Figure 6:
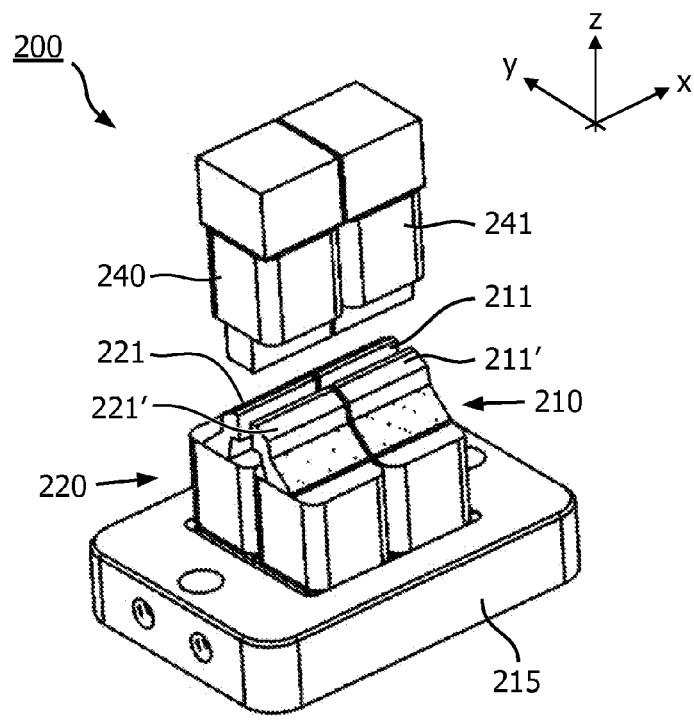
FIG. 6 shows the electromagnets of FIG. 5 separately in a perspective view.

In FIGS. 5 and 6, an alternative embodiment with more closely spaced electromagnets 210, 220 is illustrated in a top view and a perspective, respectively. Here the distance D (in x-direction) between the electromagnets is smaller than about half the distance A (in y-direction) between the pole tips. For the above mentioned typical values of A (about 1 mm) and L (about 5 mm), the distance D may preferably be about 0.2 mm.

An advantage of this embodiment is that the field of view of the optics can be smaller, for example about 7 mm. However, crosstalk (or mutual magnetic influence) of the electromagnets 210, 220 will not be negligible anymore, which must be taken into account and suitably be dealt with. This can for instance be done by operating the (immediately) neighboring poles of different electromagnets oppositely, as indicated in FIG. 5 by the symbols "N" for the North Pole and "S" for the South Pole of the pole tips. The operation of the two electromagnets 210, 2210 should therefore be synchronized accordingly.

Figure 7:
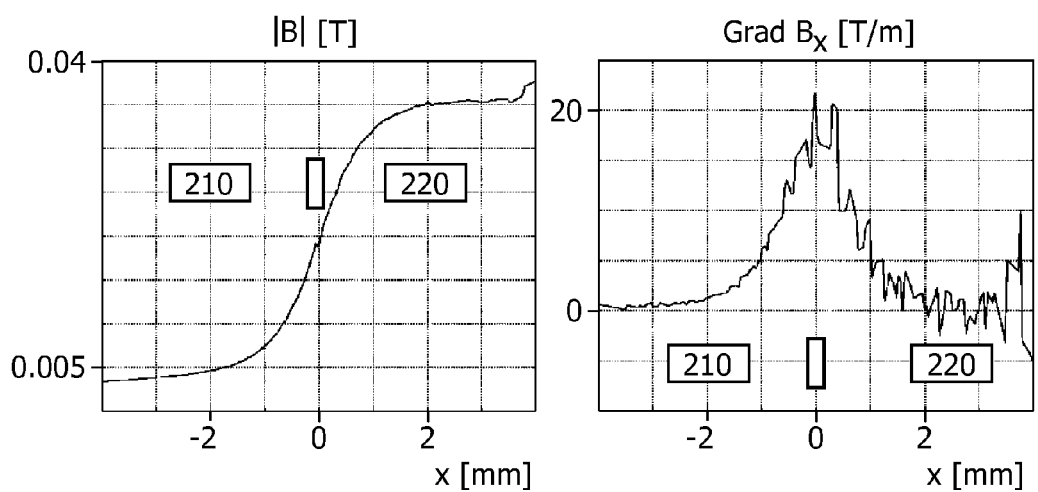
FIG. 7 shows recordings of the magnetic field and its gradient for the arrangement of FIG. 5.

FIG. 7 shows two diagrams representing the magnetic flux density B (left) and its gradient and x-direction (right) for the configurations of FIGS. 5 and 6 in dependence on the lateral position x when only the right electromagnet 220 is on.

Figure 8:
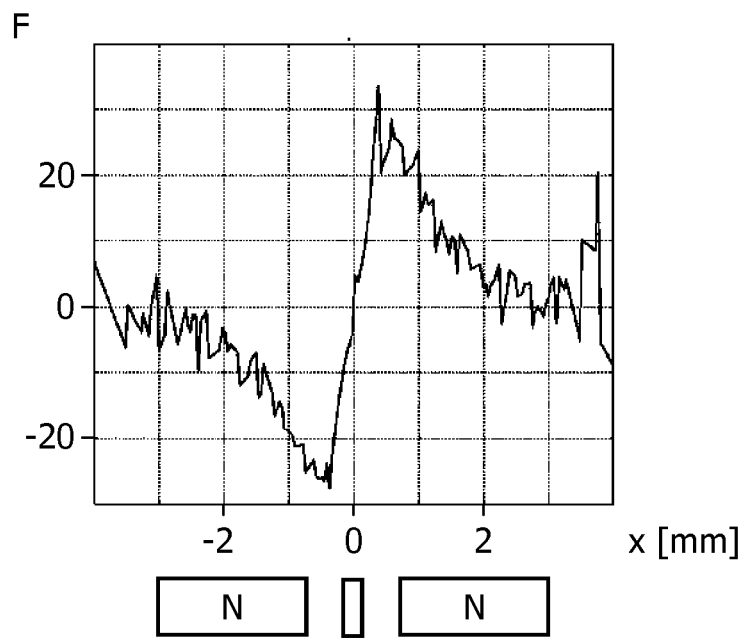
FIG. 8 shows the magnetic force in x-direction acting on a magnetic particle if neighboring poles have the same polarity.

FIG. 8 shows the magnetic force F acting on a magnetic particle in x-direction for the configurations of FIGS. 5 and 6 if neighboring poles 211 and 221 (as well as 211' and 221') are operated to have the same polarity. Strong repelling forces in the gap between the two electromagnet 210 and 220 result in a depletion of this region with magnetic beads.

Figure 9:
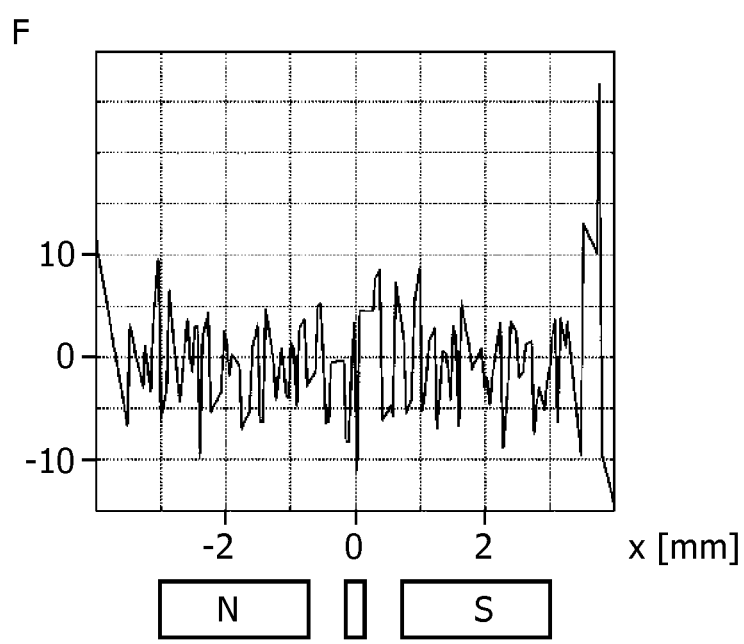
FIG. 9 shows the magnetic force in x-direction acting on a magnetic particle if neighboring poles have opposite polarity.

FIG. 9, on the contrary, shows the magnetic force F acting on a magnetic particle in x-direction if neighboring poles 211 and 221 (211' and 221') are operated to have opposite polarities. Forces are approximately zero along the x-axis in this case.

As the "opposite-polarity mode" of FIG. 9 yields an even distribution of magnetic beads, it is usually preferred in an assay. However, if repulsion of magnetic beads is desired, the "same-polarity mode" of FIG. 8 may be used as well. In general, both modes may be mixed with predetermined (temporal) fractions to yield any combination of effects.

Practical experience indicates that for every specific assay which shall be done with a sample a protocol should be used that was specifically designed to improve sensitivity. This means that in the order to increase sensitivity, analysis of the different analytes should be performed in separated sample chambers provided with independent actuation zones. This requirement is favorably fulfilled by the configurations disclosed above, which allow the attraction of magnetic particles (e.g. superparamagnetic beads) in two or more independent zones. Due to the separation of the sample chambers cross reactivity effects are avoided and assay conditions can be optimized individually.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A sample-processing device with means for generating a magnetic field (B) in a first and a second sample chamber (SC1, SC2) that are located adjacent to each other in an x-direction and have a bottom extending in said x-direction and in a y-direction which is substantially perpendicular to the x-direction, comprising:
   a) a first electromagnet with a core having a horse-shoe shape and with a first pair of poles (111, 111', 211, 211') that can be disposed below the first sample chamber (SC1) next to each other in said y-direction;
   b) a second electromagnet with a second pair of poles (121, 121', 221, 221') that can be disposed below the second sample chamber (SC2) next to each other in the y-direction;
   c) a control unit for controlling the first and the second electromagnet individually.

2. A method for processing a sample with a sample-processing device in a first and a second sample chamber (SC1, SC2) that are located adjacent to each other in an x-direction and have a bottom extending in said x-direction and in a y-direction which is substantially perpendicular to the x-direction, comprising:
   a) disposing below the first sample chamber (SC1) a first electromagnet with a core having a horse-shoe shape and with a first pair of poles (111, 111', 211, 211') which are arranged next to each other in said y-direction;
   b) disposing below the second sample chamber (SC2) a second electromagnet with a second pair of poles (121, 121', 221, 221') that are arranged next to each other in the y-direction;
   c) controlling the first and the second electromagnet individually to generate a magnetic field (B) in the first and/or the second sample chamber (SC1, SC2) such that neighboring poles (211, 221; 211', 221') of different electromagnet have in average opposite polarity for a predetermined percentage of time.

3. The device according to claim 1 characterized in that an exchangeable cartridge hosts the first and second sample chamber (SC1, SC2).

4. The device according to claim 1 characterized in that the first and the second sample chamber (SC1, SC2) are physically separated from each other.

5. The device according to claim 1 characterized in that the second electromagnet comprises a core with a horse-shoe shape.

6. The device (100) according to claim 1 characterized in that the pairs of poles (111, 111', 121, 121') of the first and second electromagnet, respectively, are separated in x-direction by a distance (D) that is larger than the distance (A) between the poles of one pair, preferably by a distance (D) that is more than about 1.2 mm.

7. The device according to claim 1 characterized in that the pairs of poles (211, 211', 221, 221') of the first and the second electromagnet, respectively, are separated in x-direction by a distance (D) that is less than half the distance (A) between the poles of one pair, preferably by a distance (D) that is less than about 0.5 mm.

8. The device according to claim 1 characterized in that neighboring poles (211, 221; 211', 221') of different electromagnets are operated to always have opposite polarity.

9. The device according to claim 1 characterized in that the device comprises a sensor module for detecting particles (1) in at least one of the sample chambers (SC1, SC2) particularly at a sensing surface adjacent to the electromagnets.

10. The device or the method according to claim 9, characterized in that the particles (1) are detected with an optical, magnetic, mechanical, acoustic, thermal or electrical sensor module.

11. The device or the method according to claim 10, characterized in that the sensor module comprises a light source that illuminates sensing regions (SR1, SR2) of both the first and the second sample chamber (SC1, SC2).

12. The device or the method according to claim 10, characterized in that the sensor module comprises a light detector, particularly an image sensor, that measures light coming from sensing regions (SR1, SR2) of both the first and the second sample chamber (SC1, SC2).

* * * * *